United States Patent
Cook et al.

[11] Patent Number: 5,934,099
[45] Date of Patent: Aug. 10, 1999

[54] TEMPERATURE CONTROLLED CONTAINER

[75] Inventors: Sanford L. Cook, Ocean; Joseph N. Villa, Hazlet, both of N.J.

[73] Assignee: TCP/Reliable Inc., Edison, N.J.

[21] Appl. No.: 08/901,570

[22] Filed: Jul. 28, 1997

[51] Int. Cl.⁶ .............................. B65B 63/08; F25D 3/08
[52] U.S. Cl. ............................. 62/457.2; 62/60; 62/371; 206/570
[58] Field of Search ................ 62/60, 371, 372, 62/457.1, 457.2, 457.7, 530; 206/570

[56] References Cited

U.S. PATENT DOCUMENTS

| | | | |
|---|---|---|---|
| 5,058,397 | 10/1991 | MacDonald | 62/457.2 |
| 5,181,394 | 1/1993 | Schea et al. | 62/371 |
| 5,186,900 | 2/1993 | Jensen et al. | 422/104 |
| 5,355,684 | 10/1994 | Guice | 62/54.2 |
| 5,419,152 | 5/1995 | Silber | 62/372 |
| 5,600,958 | 2/1997 | Henning et al. | 62/60 |

*Primary Examiner*—William Doerrler
*Attorney, Agent, or Firm*—Jonathan B. Schafrann

[57] ABSTRACT

A container is disclosed for storing and transporting vessels containing a composition susceptible to physicochemical alteration upon changes in temperature above or below a specified temperature range. It comprises a first housing having a vessel holder, and a heat sink disposed within the first housing. A second housing encloses the first housing, the second housing is preferably comprised of a metallic material and is of a double-walled construction.

6 Claims, 5 Drawing Sheets

TEMPERATURE CONTROLLED CONTAINER

FIELD OF THE INVENTION

The present invention relates generally to a container for transporting and storing labile materials, and more specifically to a container for transporting and storing temperature-sensitive materials and frangible vessels.

BACKGROUND AND SUMMARY OF THE INVENTION

There are significant problems attendant to transporting and storing thermally-sensitive materials like pharmaceuticals or biologicals. The problem of temperature maintenance is compounded by the hazard of breakage when a glass container retains the temperature sensitive material. Further, the incidence of spoilage and breakage dramatically increases when one conveys containers over long distances. While shippers can deliver refrigerated containers over long distances, transporting labile payloads through normal shipping channels, without refrigeration, often results in cargo loss from exposure to extremes in temperatures. It should be noted that, while most people believe that refrigeration is a preferred method for storing and transporting pharmaceuticals, exposure to sub-ambient temperatures often results in the loss of many medications. The objective therefore for transporting pharmaceutical preparations, is to maintain a payload within a specified temperature range.

During shipping, a single manufacturing "run" of product may face unexpected exposure to extremes in temperature. For example, a delivery truck in the southwestern part of the United States may encounter the elevated temperatures of the deserts, while another shipment of the same medicine may suffer freezing temperatures of the northeast. A shipment of pharmaceuticals stored on the tarmac prior to loading on an aircraft may endure highly elevated temperatures for extended periods of time. On the other hand, once loaded in the cargo hold of an aircraft the same pharmaceuticals are often exposed to sub-freezing temperatures for prolonged periods during flight. Without a means of temperature control, the contents of traditional containers are at the mercy of the elements.

Hence, there has been a longstanding need to provide packaging that can maintain its contents at a desired temperature range while comporting with the size or weight limitations of shipping and storage.

There are many containers for transporting medicines, biologicals, and temperature-sensitive materials. Containers in accordance with the prior art are designed for transporting a particular product like insulin or nitroglycerin. Heretofore, there has been no single container that can successfully transport a variety of labile materials. In order to fulfill the requisites for multi-product shipping, a container must be adapted to transport not only nitro-glycerin or an oncology drug, but also other materials like biologically active proteins which may be susceptible to irreversible physico-chemical alteration upon freezing or medicaments which lose efficacy upon exposure to elevated temperatures. The problem remaining unsolved is to design a container capable of maintaining its inner environment at a constant temperature, notwithstanding temperature changes outside the container, while being dimensionally acceptable to established shipping standards.

Another problem, long recognized yet remaining unsolved, is to provide a container that not only maintains the product safely during shipping, but also possessing the added advantage of providing a temperature controlled environment at the point of usage. For example, the container must safely hold an oncology drug in a doctor's office or insulin vials when transferred to the patient.

STATE OF THE PRIOR ART

The developing technologies relating to recombinant DNA and biologically active materials like peptides, oncology drugs, new-generation pharmaceuticals, proteins and glyco-proteins for research and therapeutic use present unique problems. Biological products are extremely potent and are frequently supplied as dilute aqueous solutions of the active ingredient combined with small quantities of pharmaceutically acceptable adjuvants and carriers. Evidence indicates freezing the solution can generate physico-chemical alterations which are not immediately reversible upon thawing. These changes could potentially affect the biological potency of the products which have been subjected to freezing. In the case of pharmaceutical preparations, exposure to elevated or lowered temperatures may render the preparation ineffective or toxic. Therefore, a common problem encountered with transporting and storing pharmaceuticals is to maintain the pharmaceutical preparation within a constant temperature range.

In addition, to the problems encountered with shipping multiple containers of a given pharmaceutical preparation, the end user is confronted with the same problems of maintaining a required temperature range. Whether it is a doctor treating many patients with the same drug, or the patient who must transport and store the medication upon filing a prescription, it is necessary to maintain the medication at a temperature range that maintains efficacy. For example, insulin preparations must be available to the stabilized diabetic and be maintained within a temperature range of from 40° F. to about 75° F. The daily self-administration of insulin includes using insulin syringes. Moreover vials which contain insulin are preferably constructed from a frangible material like glass thereby adding to the problems of carrying insulin.

The prior art is rife with various container designs fashioned from polymer materials, alone or in combination with cardboard or particle-board components.

Shipping boxes with insulated interiors run the gamut from ubiquitous "food-coolers" to esoteric single vessel transport units. For example, a cardboard box filled with foam "peanuts" surrounding a second cardboard box holding the medicament is but one common embodiment, albeit without the ability to maintain a controlled temperature environment. Other examples embrace plastic containers within which open cell or closed cell foam substantially sized the same as the interior contains a cutout adapted to receive a second box - the second box contains the medication. Still another commonly employed container is an inner vessel surrounded by a space which has been evacuated of air and surrounded by a second or outer wall (the common Thermos® bottle is well known).

Persons seeking to transport labile materials, which must be preserved in a frozen state, have used ice and dry-ice for maintaining temperatures sufficient to keep the samples in a frozen condition. Unfortunately, dry-ice preparations are of limited utility due to rapid evaporation, the undesirable release of carbon dioxide gas in closed vehicles, and the movement by many carriers and countries against materials which release gases like carbon dioxide. Moreover, the use of ice and dry-ice creates the untoward risk of introducing a toxic contaminant or pathogen. Unless precautions are taken to keep the melting ice and the aqueous product in a position removed from direct contact with the cooling agent, pathogens from the ice or from the surrounding area may contaminate the product.

Some transportable containers rely on refrigeration units to maintain sub-ambient conditions. With these systems a power failure, which might proceed undetected, could prove fatal to the efficacy of the preparation. As a general rule, any container which requires interaction and vigilance by the user or carrier will likely fail in the field.

While most people are familiar with spoilage due to exposure to heat, or to freezing, maintaining a constant temperature within a prescribed range is now recognized as a most desirable objective. There is a vast array of pharmaceutical preparations that must be maintained within a specified temperature range. For traditional pharmaceuticals, the preferred temperature range may be from about 40° F. to 80° F. Newer drugs and biological preparations require an extremely narrow temperature range of ±3 degrees F of a specified temperature to prevent spoilage. Newer oncology drugs and biologicals are exquisitely sensitive to small changes in temperature. Therefore, in order to be effective, a container must inherently prevent changes in outside temperatures from affecting interior temperatures and the preparation contained therein.

As an overall precept, prior art containers teach the construction of containers for maintaining contents at sub-ambient/supra-ambient temperatures.

U.S. Pat. No. 5,181,394 issued Schea, III et al. discloses a previous attempt to provide a shipping and storage container adapted to maintain vials of liquid in a refrigerated, but not frozen state. The container comprises an outer side wall having the shape of a rectangular open tray and an inner side wall having a number of wells to accommodate a number of vials. The inner and outer side walls are dimensioned and shaped to nest the inner side wall component within the outer side wall component. A phase change material comprising a freshly prepared mixture of water and 2% by weight of self-gelling carboxymethylcellulose is provided between the inner and outer side walls.

A freeze indicator is positioned within the container and exhibits a color change upon being subjected to temperatures below a predetermined level.

U.S. Pat. No. 5,355,684 issued to Guice discloses a shipping container for the cryogenic shipping or storage of biologic materials. Further, this invention utilizes a plurality of "heat sinks" disposed within an insulated container. The heat sink material is preferentially composed of a phase change material that is first frozen and as it thaws, absorbs free heat to keep the sample inside the vessel in a frozen condition.

U.S. Pat. No. 5,058,397 issued to MacDonald discloses a storage container where micro-centrifuge tubes are embedded into a coolant matrix of gel. Overlying the embedded tubes is a gel contained in an envelope within a closure means which is comprised of an envelope of gel.

U.S. Pat. No. 4,250,998 issued to Taylor discloses a container for transporting insulin and syringes wherein there is an insulated container with a plurality of cavities. The inner cavities are to be filled with water for freezing, while the outer cavities are designed to house the syringes.

U.S. Pat. No. 3,807,194 issued Bond discloses a thermodynamic container having a double walled plastic shell and a heat exchanging cup retained therein. The assemblage is meant to be resistant to shock and uses a variety of eutectic materials to maintain container temperature as a result of said material reaching its heat of fusion. The container takes advantage of the energy available from the heat of fusion or crystallization. Furthermore, it is the temperature of the material retained within the cup that provides the energy necessary for maintaining the system. By immersing the material like a can of food in boiling water for a specific period of time, the container will then maintain the contents of the can at an elevated temperature for many hours later. Obviously, for materials that are sensitive to changes in temperature this charging operation would prove to be fatal.

OBJECT OF THE INVENTION

It is the object of the invention to provide a container for storing and shipping temperature sensitive materials at a desired temperature range.

It is another object of the present invention to provide a container that may be used not only during shipping, but also as a container for usage by an end user.

Yet another object of the present invention is to provide a container for maintaining its contents within a temperature range of about a ±3 degree variance from a given value.

Another object of the present invention is to provide a container where the contents can be maintained at a given temperature range for extended periods of time.

Yet another object of the present invention is to provide a container that has a high degree of transportability and is easily stored.

SUMMARY OF THE INVENTION

A container according to the present invention provides for storage and shipping of multiple vials containing labile materials that are susceptible to physicochemical alteration upon freezing or upon exposure to elevated temperatures. The container comprises a first housing which is open on one end and closed on the other and preferably is cylindrical in shape. The first housing retains a vessel holder. The vessel holder, is thin, planar, and is preferably circularly-shaped to coincide with the overall shape of the first housing. The vessel holder presents a plurality of downwardly depending tubular retention chambers open on one end, closed on the other, and adapted to receive a like number of vessels or vials therein. The inside area of the first housing is filled with a phase-change material, the material occupying substantially all of the inner space and being interposed in communication with the downwardly depending tubular retention chambers. The vessel holder is affixed on and encloses the first housing so as to confine the phase change material therein. A second housing of a substantially greater dimension is provided and adapted to receive the first housing. The second housing, which emulates the shape of the first housing, is preferably constructed to include an inner wall and an outer wall, so that the walls provide an annular space. The annular space created thereby is preferably evacuated of air. The second housing is of a size and shape to accept the first housing therein.

A lid provides closure of the second housing and is removably retained thereon. The lid is adapted to be removably affixed to the second housing and may, as preferred embodiments, be insulated or possess a dual wall construction with an evacuated inner area like the second housing. The lid means is removably retained and provides access to extract the individual vessels without necessitating the removal of the first housing and the vessels retained therein. The user therefore has easy access to effect withdrawal of the vessels or vials.

Both first and second housings are preferably cylindrical and elongated in overall shape. The first housing nests within the second housing, and is removably retained therein.

Within the first housing is a heat sink, comprising a thermal energy-absorbing phase-change material. The heat sink, which is preferably a phase-change material, occupies substantially all of the area within the first housing and gives rise to an insulating and moderating space.

The vessel holder, which is preferably planar and circular, acts as a means to close the open end of the first housing. The vessel holder is adapted to removably retain at least one vessel or vial suspended within elongated tubular retention chambers and disposed within the cell created by closure of the first housing. The elongated tubular retention chambers are substantially in communication with the heat sink which is preferably a phase-change material. Desirably, the resulting array of apertures is essentially in an equidistant relation to one another.

Located centrally to the apertures is a stop and handle means preferably disposed on the upper surface of the vessel holder. The handle and stop means provides an upper boundary to protect the vessels and when in communication with a closure or closure of the second housing prevents the vessels from moving up and out of the tubular retention chambers of the vessel holder. The stop means, acting as a handle, allows the user to withdraw the first housing from the second housing and the vessels retained therein.

The second housing surrounds the first housing, the housing comprising a double-walled construction. The space between the first and second walls of the second housing is preferably evacuated so as to constitute a vacuum within the space. Alternatively, an insulating gas, solid, liquid, or gel may be contained in the inner space. Additionally, both first and second housings are fashioned from non-porous and insulating materials. Preferredly, the second housing is preferably fashioned from a metallic material.

BRIEF DESCRIPTION OF THE DRAWINGS

Further features, objects and advantages will become evident from the following detailed description of the preferred embodiments of the present invention taken in conjunction with the accompanying drawings, in which.

DETAILED DESCRIPTION

Figure 1:
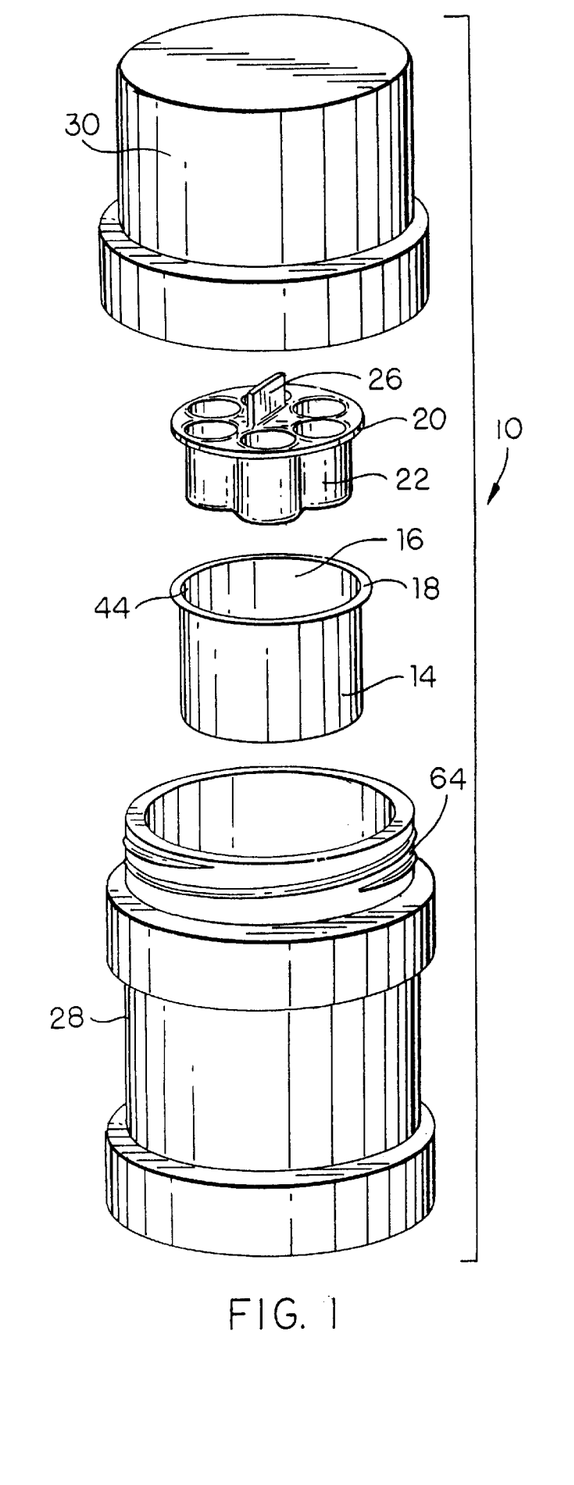
FIG. 1 is an exploded view of a temperature controlled container according to the invention.
Figure 7:
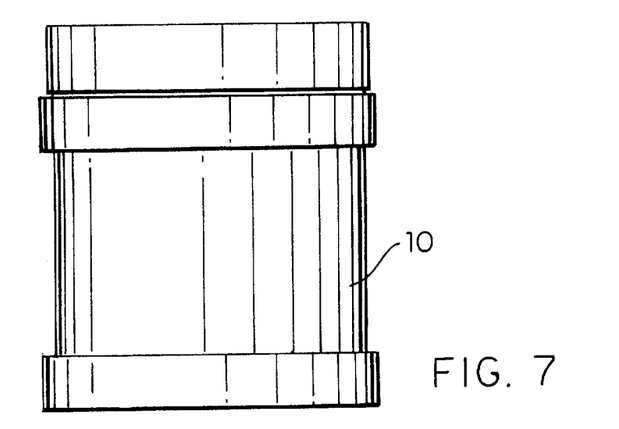
FIG. 7 is an elevational view thereof in a closed condition.

Turning now to the drawings wherein like numerals refer to like parts throughout, FIGS. 1 and 7 depict a temperature controlled container for transporting and storing temperature-sensitive materials, said container being generally referred by the numeral 10.

Container 10 is preferably cylindrical in overall shape, as best shown in FIGS. 1 and 7, although triangular, rectangular or multiple sided constructions can be operatively substituted without loss of efficacy.

In accordance with the present invention and particularly with attention to FIGS. 1 and, a first housing 12, arises from the communication of wall 14 and base 42. In a preferred embodiment of the present invention, the resulting overall shape is essentially cylindrically elongated. First housing 12 is closed on one end a bottom end and forming base 42 and open on the opposing end forming opening 44.

Figures 2, 3, 4:
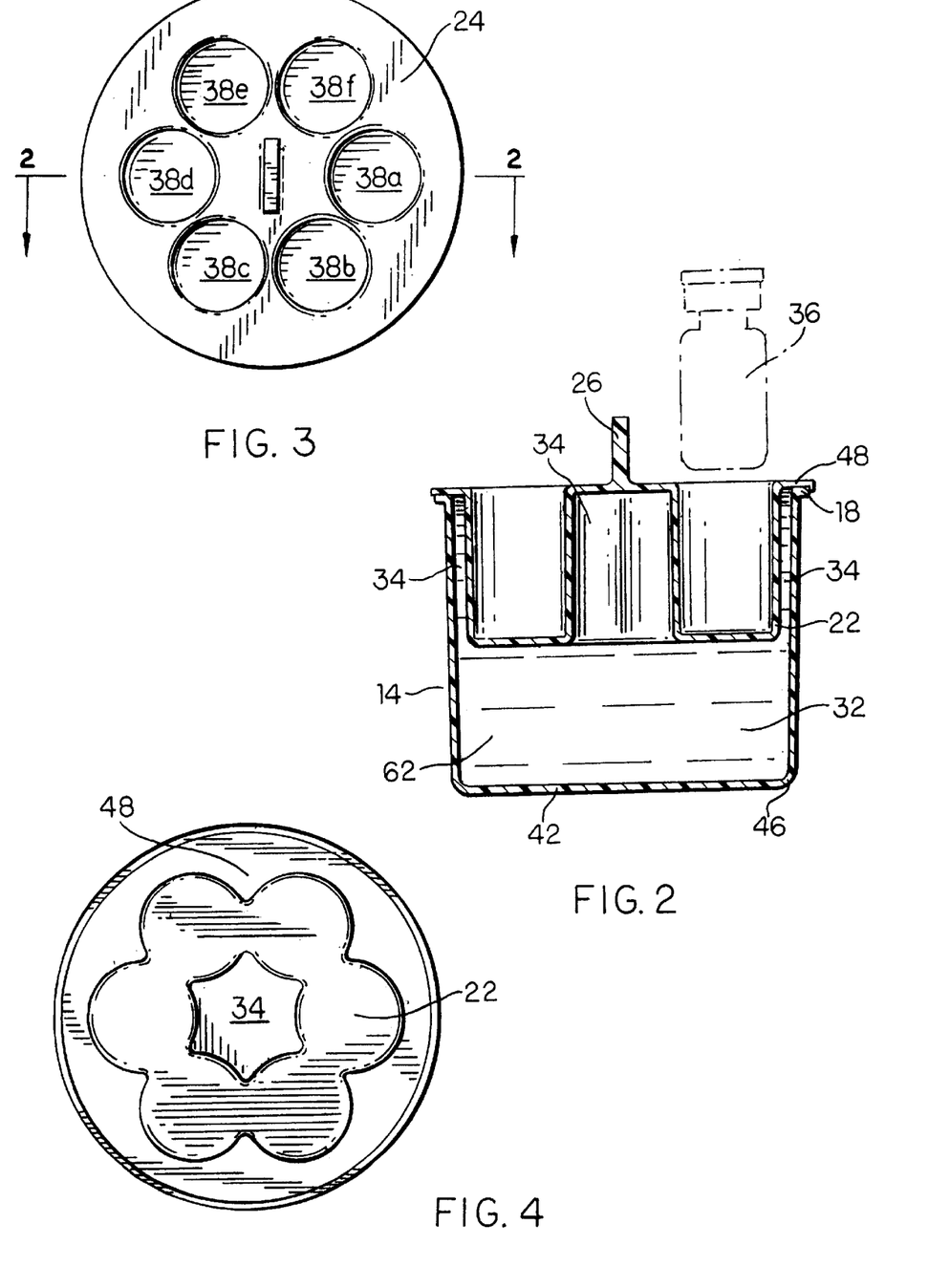
FIG. 2 is an elevational view taken in cross-section of a vessel holder and first housing.
FIG. 3 is a top plan view of a vessel holder.
FIG. 4 is a bottom plan view thereof.
Figure 5:
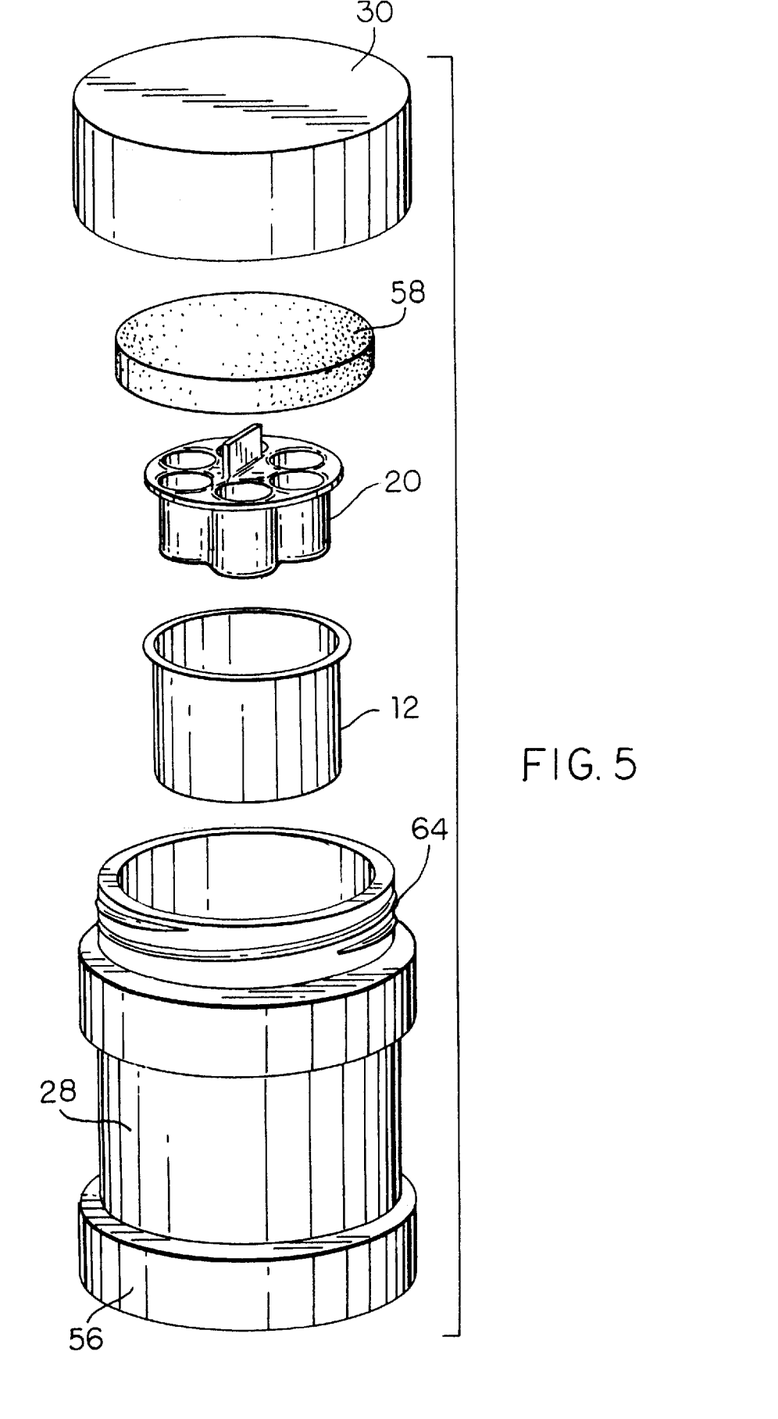
FIG. 5 is an exploded view of a temperature controlled container showing an alternate embodiment with an insulating insert.
Figure 6:
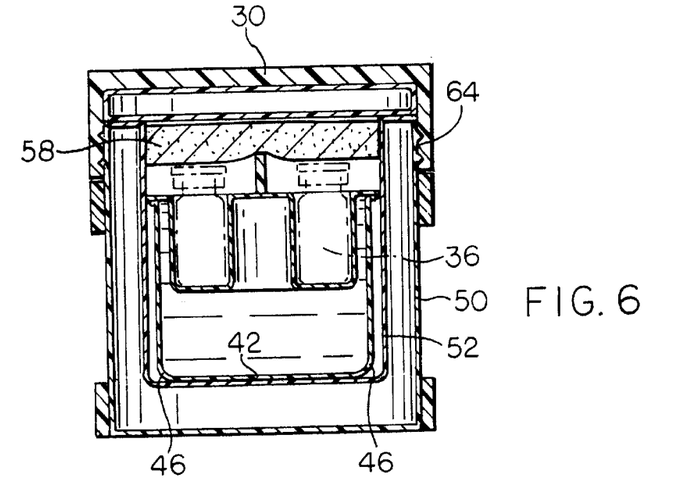
FIG. 6 is a cross-sectional view thereof in a closed condition.

Turning to FIGS. 1, 2 and 6, base 42 is of the approximate dimension of opening 44 located opposite therefrom. Opening 44 terminates in flange 18 which encircles opening 44 at its outermost boundary creating a communication surface for placing vessel holder 20 and anchoring it thereupon, as illustrated in FIG. 2. Once placed over opening 44, vessel holder 20 creates closure of first housing 12 and gives rise to inner cell 62.

Base 42 of first housing 12, as depicted in FIGS. 2 and 6 desirably has a rounded area at shoulder 46. Shoulder 46 permits first housing 12 to be placed and then withdrawn from second housing 28 with maximum ease. Furthermore, shoulder 46 and the preferred rounded architecture of base 42 provides for increased strength upon filling without the need for ancillary support ribs or buttressing. Rounded base 42 aids the user in placing inner housing 12 in second housing 28, and extracting it therefrom.

Cell 62, created by the aforesaid communication between base 42, and wall 14 and its closure by vessel holder 20, provides, as depicted by FIG. 2, a receptacle for heat sink 32. Spaced apart from one another and in communication with heat sink 32 are downwardly depending tubular retention chamber(s) 22, said downwardly depending tubular retention being disposed within cell 62. Space 34, which represents an area free from heat sink 32 and the phase change material is preferably occupied by air or other gas. Space 34, apart from its temperature modulating properties also provides an area to absorb the expansion of the phase change material of heat sink 32.

As illustrated by FIGS. 2 and 6, a plurality of vessels 36 are removably retained within corresponding downwardly depending tubular retention chamber(s) 22. As depicted in FIGS. 1, 3 and 4, the overall conformation of downwardly depending tubular retention chamber(s) 22 is preferred as an overall radially arrayed downwardly depending arrangement, which is circularly-shaped said retention chambers may be individually formed or as in the referenced figures molded as one.

As stated heretofore, in a preferred embodiment, while the bottom margin of first housing 12 is closed by base 42, the top of wall 14 terminates in an outwardly projecting flange 18. Pursuant to FIG. 2, flange area 18 is in communication with underside area 48 of vessel holder 20. To provide closure, flange 18 of vessel holder 20 is preferably sealed as by sonic welding or by a therm-forming operation with undersurface 48 of vessel holder 20. Other constructions that result in vessel holder 20 being irreversibly retained on first housing 12 could be operatively substituted. Vessel holder 20 is preferably sonically welded to first housing 12, after deposition of heat sink 32 therein.

Pursuant to another preferred embodiment and FIG. 2 flange 18, extends outwardly radially from the upper extent of wall 14. Surface 48 may have a downward projection so that vessel holder 20 rests upon 48 for ease in sealing. As a result flange 18 and surface 48 can engage one another to hold the closure 20 to the base 12 prior to sealing.

In a preferred embodiment as shown in FIG. 2, there is at least one heat sink 32. Heat sink 32 cooperatively provides a media to absorb temperature changes. For the present invention, the material which comprises heat sink 32 is preferably a phase-change material. Such materials can absorb a tremendous amount of heat energy during their transition between phases thereby maintaining the surrounding temperature at an essentially constant value. By example, when preserved in a frozen state, the product of net specific heat and density would represent an inverse logarithmic relationship. Hence, once the material which has been in a frozen condition reaches the point of freeze/thaw, the temperature remains substantially constant within a temperature plateau, until a complete change of phase occurs. This temperature plateau allows for great amounts of heat to be absorbed at a constant rate before the transition between phases takes place. This phenomena helps maintain the container temperature constant.

Heat sink 32 is preferably constructed from a phase-change material such as a carboxymethylcellulose gel, having a freezing temperature of approximately −1° C. Other materials for constructing heat sinks include phenols, salts, glycols, starches, alcohols, and acetones and aqueous and non-aqueous combinations thereof. It is further preferred that the phase change material is a gel.

As described hereinabove, the heat sink material may be chosen from a variety of materials, based on their transition or phase-change characteristics and the desired temperature at which the sample is to be maintained. For example, some of the alcohol or glycol gels may be operatively substituted for maintaining very low temperatures since their freezing points are extremely low. Alternately, one can heat the phase change material to impart a supra-ambient temperature to the contents of vessels 36. In yet another embodiment by maintaining the phase change material at an ambient temperature the temperature of vessels 36 may be maintained within ambient limits. As a general rule the more prolonged transition between phases is preferred.

Although, it is preferred that heat sink 32 be disposed within inner cell 62, one can separate heat sink 32 from vial holder 20 by enveloping the heat sink in a covering or by segregating it by the use of an annular wall means. A preferred embodiment resides in depositing the phase change material within cell 62 as depicted in FIGS. 2 and 6, and allowing it to expand and contract free from space restriction.

Other embodiments or materials could be operatively substituted for a gel. For example, materials like dry-ice, certain salts and highly esoteric super conductor/insulator which remain solid through their "phase change" would obviate the need for a gel material of heat sink 32.

As a further alternate embodiment, inner wall 16 of first housing 12 may be coated with a reflective surface to further enhance the resistance of the container to temperature changes. Hence, in accordance with FIG. 1, inner surface 16 of wall 14 could be mirrored with a reflective mylar, polymer or reflective coating applied thereto.

Wall 14, base 42 and vessel holder 20 are preferably formed from a thermoplastic polymer component like polyvinyl chloride, styrene, PETG or another closed cell polymer. When constructed as by injection molding or by another thermo-forming method said wall 14 and base 42 are preferably integral.

Wall 14, base 42 and vessel holder 20 are the first barriers to prevent temperature changes within the container. The thermoplastic polymer is non-porous, insulating and retards heat transfer. Therefore, depending on the thickness of the polymer there will be an insulating or R factor, while the material itself will by definition facilitate or retard heat transfer by virtue of its K factor. Not only does the non-porous material retard interior temperature changes through radiation, but also the inherent insulation rating of the material itself curbs heat transfer through conduction. Finally, convection caused by air passing over the container and the non-porous surface has little effect on the contents or the interior temperature.

Second housing 28 is preferably cylindrical, and in accordance with FIGS. 1, 5, 6, 6a and 8 is dimensionally larger than first housing 12. As depicted in FIG. 6 the construction of second housing 28 is at least double-walled having an inner wall 52 and an outer wall 50, said inner and outer walls 52 and 50 being in a closed conformation, and creating an annular chamber 54. Second housing 28, although substantially larger than first housing 12, is closed on one end and open on the other.

As first housing 12 has upstanding wall 14 and base 42, second housing 28 has upstanding walls 50 and 52 and a base 56 and. Annular space 54 created by the communication of inner wall 52 and outer wall 50, is preferably evacuated, but may be filled with an insulating material, like a closed cell polymer, or a heat sink. Second housing 28 is preferably constructed from a metallic material, while first housing 12 is preferably constructed from a rigid thermoplastic polymer. Second housing 28 is preferably constructed from stainless steel, although other metallic and non-metallic materials may be operatively substituted.

As a preferred embodiment, and in accordance with FIGS. 1, 5, 6, 7, and 8 a closure means 30 may be a lid or other a threaded assembly of upstanding male thread 64 and a channel for receiving the thread 66. Said closure 30 possessing a base, upstanding walls and a threaded area to secure closure 30 to second housing 28. Closure means 30, may be constructed as a lid that snaps on or interlocks. In addition, closure means 30 may also contain a double walled construction like second housing 28. The annular space within the lid may be evacuated or insulated.

Thus, when container 10 endures an aberrant temperature either above or below the critical temperature range of the sample within vessels 36, a moderating effect is produced by the interaction between not only first and second housings 12 and 28, but also by the moderating influence of heat sink 32. A large quantity of heat energy relative to the mass of heat sink 32 may be absorbed prior to a change in the temperature of the sample retained within vessels 36. Therefore, only after greatly prolonged exposure, which would exceed reasonable travel/storage times, would there be a significant change in sample temperature relative to temperature changes in the external environment.

Heat sink 32 in combination with the first housing 12 and second housing 28 provides a thermal damping effect against temperature changes in the environment of the container 10. Using a total weight of carboxymethylcellulose of 6.5 ounces, container 10 should can resist exposure to drastic changes in outside temperature.

As depicted in FIG. 2, planar surface 24 preferably contains a plurality of apertures 38a–f corresponding to the number of downwardly depending, elongated tubular retention chambers and being adapted to receive a like number of vials therein. A stop and handle means 26 is preferably located at a central point and furnishes said plurality of apertures 38a–f a point for their arrangement in equidistant relation thereto. In its preferred embodiment said downwardly depending elongated retention chambers 22 are essentially shorter in length than the vessels which are retained therein, allowing for ease in the extracting vessel(s) 36. In accordance with FIG. 2, the overall preferred arrangement of the apertures is in an essentially circular fashion disposed around a central stop and handle means 26.

As best depicted in FIG. 6, disposed in a central location and in an upstanding attitude, stop and handle mean 26 protects vessels 36 by preventing their upward ejection from downwardly depending elongated tubular retention chamber (s) 22. In addition said stop and handle member 26 prevents compression damage by providing a rigid upper margin, which minimally exceeds the height of vessel(s) 36. Most importantly, stop and handle means 26 functions as a handle, so that the user can obtain a purchase and withdraw first housing 12, from second housing 28, when first housing 12 is in a loaded or unloaded condition. It is preferred that stop and handle means 26 is upstanding and solid although other configurations like an inverted unshaped upstanding appendage may be operatively substituted.

Turning now to FIG. 6, vessel holder 20 when positioned within the first housing suspends the downwardly depending tubular elongated retention chambers 22 within heat sink 32 but above the surface of base 42 so that vessels 36 are retained thereabove. Hence, vessels 36 are protected to a substantial degree from injury from shock during the travails of shipping. Vessels 36, thus positioned, are substantially spaced from the sidewall 16 and from one another to avoid mechanical damage and breakage. It should be noted that heat sink 32 as a phase-change gel will absorb much of the offending vibratory and shock energy.

As another preferred embodiment, insulation means 58 may be employed in accordance with FIG. 6 to provide not only an insulation means but also further protection from shock and vibration. It is preferred that a closed cell polymer be used for both insulation and shock prevention. As a requirement the closed cell polymer must be easily compressible. For shock resistance only an open or closed cell easily compressible polymer may be used.

Figure 6A:
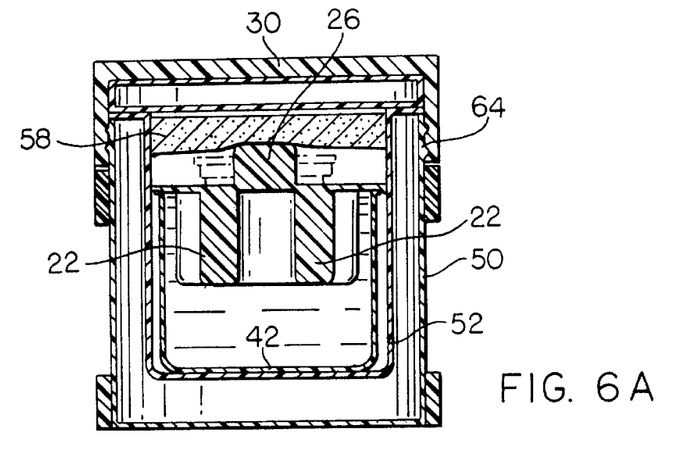

Therefore, in an embodiment according to FIGS. 6 and 6a, an insulation means 58 abuts vessel holder 20. It is preferred to use a foam like polyvinyl chloride, polyethylene pterephalate, or the like for insulation means 58.

Figure 8:
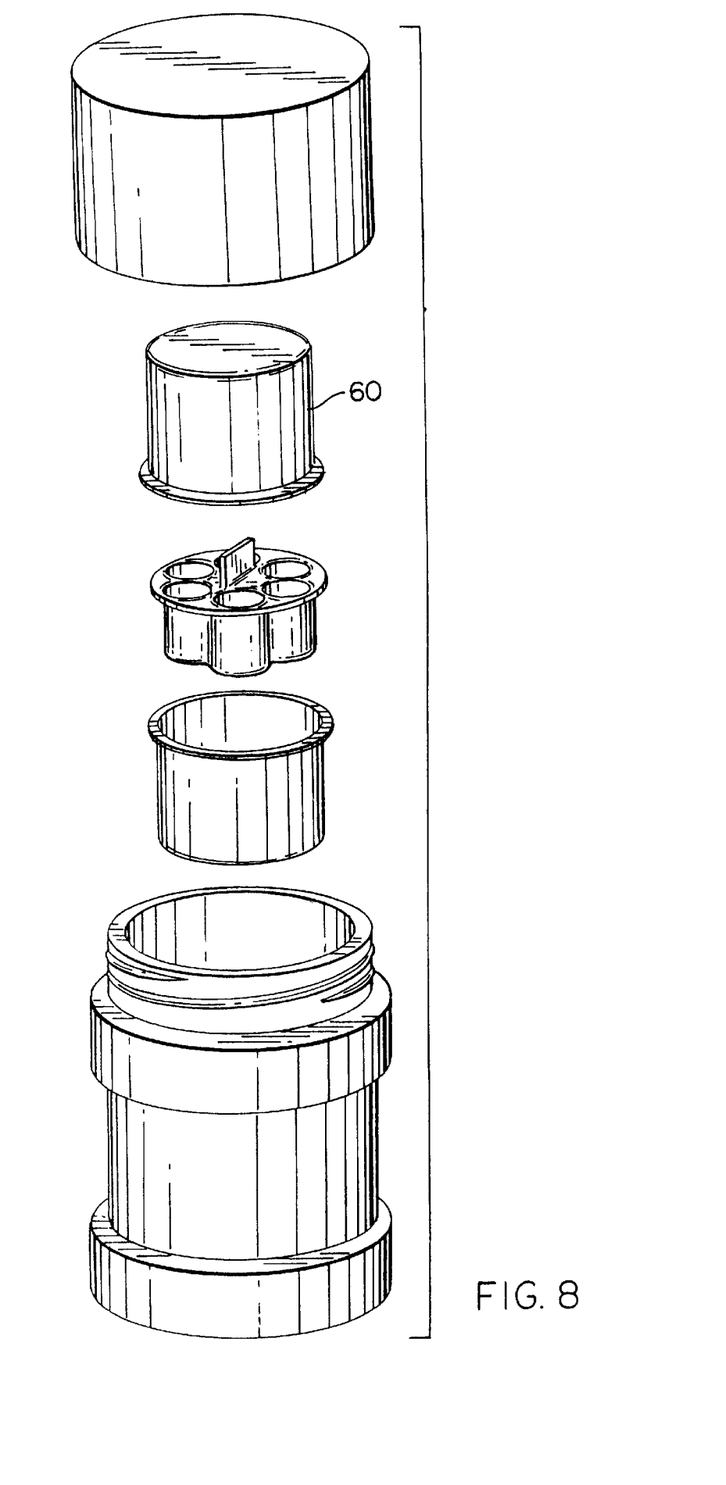
FIG. 8 is an exploded view of a temperature controlled container showing an alternate embodiment of an inverted third housing.

As an alternate embodiment, best displayed in FIG. 8 a third housing 60 may be placed in communication with first housing 12 as being place in inverted relation thereon. The inverted, reversible placement of third housing 60 on first housing 12, is effected when first housing 12 is in a loaded condition. As one can see, third housing 60 is cup-shaped and may be adapted to overlay first housing 12 along the radial margin of vessel holder 20. Third housing 60 may be adapted to communicate with radial margin of vessel holder 20 and is reversibly affixed thereon. It is preferred that third housing 60 be fashioned from a rigid thermoplastic polymer like polyvinyl chloride, polyethylene, polystyrene or the like. Third housing 60 principally functions as an insulating space to cooperate with the temperature modification aspects of heat sink 32, first housing 12, second housing 28 and closure means 30.

While the invention has been particularly described in connection with specific embodiments thereof, it is to be understood that this is by way of illustration and not of limitation, and that the scope of the appended claims should be construed as broadly as the prior art will permit.

What is claimed is:

1. A temperature controlled container comprising:
   a. an essentially cylindrical first housing closed on one end to form a base and open on the other, forming a cell therein;
   b. a heat sink disposed within said cell of said first cylindrical housing and occupying essentially the inner area of said first housing and said cell and forming an airspace therein;
   c. a vessel holder adapted to be received within said open end of said first housing, said vessel holder possessing a plurality of downwardly depending elongated tubular retention chambers closed on one end and open on the other and adapted to retain a like number of vessels therein, said downwardly depending elongated tubular retention chambers being spaced in equidistant relation to each other and being disposed in communication with said heat sink, said heat sink being a gel of carboxymethylcellulose and water;
   d. a second cylindrical housing closed on one end and open on the other, adapted to retain said first cylindrical housing, said second housing having annular walls;
   e. a stop and handle means adapted to withdraw said first cylindrical housing from said second cylindrical housing, and to define an upward boundary for said vessels; and
   f. a closure means which reversibly seals said second cylindrical housing and retains said temperature controlled container in a closed condition.

2. A stop and handle means according to claim 1 wherein said stop and handle means is located in a central location in relation to said vessels being arrayed in equidistant conformation thereto.

3. A temperature controlled container comprising:
   a. an essentially cylindrical first housing closed on one end to form a base and open on the other, forming a cell therein;
   b. a heat sink disposed within said cell of said first cylindrical housing and occupying essentially the inner area of said first housing and said cell and forming an airspace therein;
   c. a vessel holder adapted to be received within said open end of said first housing, said vessel holder possessing a plurality of downwardly depending elongated tubular retention chambers closed on one end and open on the other and adapted to retain a like number of vessels therein, said downwardly depending elongated tubular retention chambers being spaced in equidistant relation to each other and being disposed in communication with said heat sink, said heat sink being a gel of carboxymethylcellulose and water;
   d. a second cylindrical housing closed on one end and open on the other, adapted to retain said first cylindrical housing, said second housing having annular walls;
   e. a stop and handle means adapted to withdraw said first cylindrical housing from said second cylindrical housing, and to define an upward boundary for said vessels;
   f. an insulation means disposed above said vessel holder and stop means and in a nesting relationship with a closure means which reversibly seals said second cylindrical housing and retains said temperature controlled container in a closed condition.

4. An insulation means according to claim 3 wherein said insulator is a closed cell polymer.

5. An insulation means according to claim 3 wherein said insulator is chosen from the group consisting of polyvinyl chloride or polyethylene terephthalate.

6. A temperature controlled container comprising:

a. an essentially cylindrical first housing closed on one end to form a base and open on the other, forming a cell therein;

b. a heat sink, said heat sink being a gel of carboxymethylcellulose and water, and disposed within said cell of said first cylindrical housing and occupying essentially the inner area of said first housing and said cell and forming an airspace therein;

c. a vessel holder adapted to be received within said open end of said first housing, said vessel holder possessing a plurality of downwardly depending elongated tubular retention chambers closed on one end and open on the other and adapted to retain a like number of vessels therein, said downwardly depending elongated tubular retention chambers being spaced in equidistant relation to each other and being disposed in communication with said heat sink;

d. a second cylindrical housing closed on one end and open on the other, adapted to retain said first cylindrical housing, said second housing having annular walls;

e. a stop and handle means adapted to withdraw said first cylindrical housing from said second cylindrical housing, and to define an upward boundary for said vessels; and f. a third cylindrical container, open on one side and closed on the other, adapted to be received within a closure means which reversibly seals said second cylindrical housing and retains said temperature controlled container in a closed condition, said third cylindrical container residing in inverted relation over said first housing.

* * * * *